(12) United States Patent
Liu et al.

(10) Patent No.: US 10,549,542 B2
(45) Date of Patent: Feb. 4, 2020

(54) LASER PRINTER FOR PATHOLOGICAL EMBEDDING CASSETTES AND PRINTING METHOD THEREOF

(71) Applicant: SHENZHEN DFST TECHNOLOGIES CO., LTD., Guangdong (CN)

(72) Inventors: Xiaoxin Liu, Guangdong (CN); Zhongqiu Hua, Guangdong (CN)

(73) Assignee: SHENZHEN DFST TECHNOLOGIES CO., LTD., Shenzhen (CN)

( * ) Notice: Subject to any disclaimer, the term of this patent is extended or adjusted under 35 U.S.C. 154(b) by 0 days.

(21) Appl. No.: 15/776,842

(22) PCT Filed: Nov. 18, 2016

(86) PCT No.: PCT/CN2016/106344
§ 371 (c)(1),
(2) Date: May 17, 2018

(87) PCT Pub. No.: WO2017/101635
PCT Pub. Date: Jun. 22, 2017

(65) Prior Publication Data
US 2018/0326736 A1    Nov. 15, 2018

(30) Foreign Application Priority Data

Dec. 16, 2015  (CN) .......................... 2015 1 0942806
Dec. 16, 2015  (CN) ..................... 2015 2 1051761 U

(51) Int. Cl.
*B41J 29/393*  (2006.01)
*B41J 2/175*   (2006.01)

(52) U.S. Cl.
CPC ................................ *B41J 2/17546* (2013.01)

(58) Field of Classification Search
USPC .................................................. 347/102, 101
See application file for complete search history.

(56) References Cited

U.S. PATENT DOCUMENTS

| | | | |
|---|---|---|---|
| 8,857,947 B2 * | 10/2014 | Belbeck | B41J 3/543 347/19 |
| 2002/0012036 A1 * | 1/2002 | Dante | B41J 2/01 347/102 |
| 2006/0203064 A1 * | 9/2006 | Miura | B41J 2/01 347/102 |

FOREIGN PATENT DOCUMENTS

| | | |
|---|---|---|
| CN | 101804726 A | 8/2010 |
| CN | 201604362 U | 10/2010 |

(Continued)

*Primary Examiner* — Lam S Nguyen
(74) *Attorney, Agent, or Firm* — Thorpe North & Western, LLP

(57) ABSTRACT

Disclosed are a laser printer for pathological embedding cassettes and a printing method thereof. The laser printer includes an ink jet cartridge (3) filled with pigment ink, where a conveyor belt (6) is disposed below the ink jet cartridge (3), the semiconductor laser (4) is disposed on a side of the ink jet cartridge (3), and a photoelectric sensor (10) for detecting the position of an embedding cassette (1) is disposed on the conveyor belt (6). The beneficial effects brought by the printer and the printing method thereof are as follows: 1. By ejecting pigment ink droplets on an embedding cassette and irradiating the ink droplets with a laser beam from a semiconductor laser, the ink droplets have a rapid increase in temperature and are cured, so that colors are applied on a plastic surface and can be easily recognized. 2. With a combination of a guide groove and a semilunar pushing wheel, the conveyance of the embedding cassettes is implemented effectively to facilitate an operator in picking up and placing the embedding cassettes. 3. The position of an embedding cassette can be directly precisely detected using a photoelectric sensor, so as to ensure the precise (Continued)

irradiation of the ink droplets by the semiconductor laser, thereby improving the curing quality.

8 Claims, 16 Drawing Sheets

(56) References Cited

FOREIGN PATENT DOCUMENTS

| | | | |
|---|---|---|---|
| CN | 104085191 A | 10/2014 |
| CN | 104442017 A | 3/2015 |
| CN | 105751695 A | 7/2016 |
| CN | 205661152 U | 10/2016 |

* cited by examiner

LASER PRINTER FOR PATHOLOGICAL EMBEDDING CASSETTES AND PRINTING METHOD THEREOF

TECHNICAL FIELD

The present invention relates to a laser printer for pathological embedding cassettes and a printing method thereof.

BACKGROUND

A pathological embedding cassette is used as a container for preparing and storing a pathological paraffin specimen in hospitals. A pathological embedding cassette needs to be immersed in an organic solution such as formaldehyde, ethanol, and xylene during the preparation of a pathological specimen. Therefore, a pathological embedding cassette is usually made of polyoxymethylene (POM) plastic to withstand immersion in the organic solution. In order to label a pathological specimen, a specially-made pencil may be used to handwrite characters on a POM pathological embedding cassette or a label strip is manually bonded on the POM pathological embedding cassette after a specimen preparation process is completed. Manual methods have very low efficiency and a high error rate. If a pathological embedding cassette printer is used to directly print characters or a barcode on a POM pathological embedding cassette, the working efficiency can be greatly improved and human errors can be reduced. An oil solvent-based inkjet technology is frequently used in the printing industry. Characters formed via jetting can be adsorbed on the surface of a POM pathological embedding cassette, but will fall off after immersion in an organic solution such as xylene. As a result, an application requirement cannot be achieved. Water-based ink cannot adhere to the surface of a POM pathological embedding cassette at all.

In order to print characters on a POM pathological embedding cassette and enable the printed characters to resist abrasion and withstand immersion in organic solutions, a method of an ultraviolet curable ink is used previously. That is, an ink jet cartridge filled with ultraviolet curable ink is used to print characters on a pathological embedding cassette, and an ultraviolet lamp is then used to irradiate the characters, so as to cure ultraviolet ink on a plastic surface of the embedding cassette, thereby achieving the objective of enabling the characters to resist abrasion and withstand immersion in organic solutions instead of easily falling off. A method of a thermal ribbon is also used. That is, one heatable array printing head is used. The printing head is heated and pressed on the thermal ribbon, to further thermally press thermal toner on the ribbon into the surface of the POM pathological embedding cassette. In this way, the printed characters can also resist wear and withstand immersion in organic solutions.

Recently there is also a method of using a laser beam with controllable deflection to irradiate the surface of a POM pathological embedding cassette coated with a special material. A portion with a coating layer is irradiated with the laser beam, and colors change under high temperature to form characters. The method of coating with a special material is to resolve a coloring problem after POM plastic is irradiated with laser. As shown in FIG. 1, under irradiation of high-energy laser, the surface of POM plastic without a special coating layer is only thermally melted and deformed, and the colors of irradiated portions have no significant change and cannot be easily recognized.

In addition, in existing structures, the position of a POM embedding cassette is not directly detected, and an indirect position calculation manner is used for ink ejection and laser beam irradiation on the surface of the POM embedding cassette. As a result, the quality of printing and curing is affected.

SUMMARY

To overcome the deficiency in the prior art, an objective of the present invention is to provide a laser printer for pathological embedding cassettes and a printing method thereof, so that colors can be applied on a plastic surface and can be easily recognized, and the curing quality of ink droplets can be improved.

A laser printer for pathological embedding cassettes described in the present invention includes an ink jet cartridge filled with pigment ink, where a conveyor belt is disposed below the ink jet cartridge, a semiconductor laser is disposed on a side of the ink jet cartridge, and a photoelectric sensor for detecting the position of an embedding cassette is provided on the conveyor belt.

In addition, the laser printer for pathological embedding cassettes according to the present invention further has the following additional technical features. According to an embodiment of the present invention, further specifically, a magazine holder is disposed on the conveyor belt, the magazine holder is located on a side of the ink jet cartridge, and the conveyor belt passes through the magazine holder.

Further specifically, a first magazine and a second magazine are placed at an upper portion of the magazine holder, and embedding cassettes are respectively held in the first magazine and the second magazine.

Further specifically, a notch is provided on the first magazine, an elevation pushing plate is disposed at lowermost ends of the first magazine and the second magazine, a cam used to make the elevation pushing plate move up and down is disposed at a lower end portion of the elevation pushing plate, and a second micro motor for driving the cam to rotate is disposed at the cam.

Further specifically, the elevation pushing plate includes a left elevation pushing plate and a right elevation pushing plate, top portions of the left elevation pushing plate and the right elevation pushing plate respectively support the first magazine and the second magazine, two arc-shaped surfaces are disposed on the cam, and the arc-shaped surfaces are connected to each other.

Further specifically, a slide is mounted on a side of the conveyor belt, a third micro motor and a reflective photoelectric sensor are disposed at a lower portion of the slide, a semilunar pushing wheel is disposed on the third micro motor, a guide groove is disposed on a side of the pushing wheel, and a slot photoelectric sensor for detecting the angle of the pushing wheel is provided on a side of the pushing wheel.

Further specifically, a base plate is disposed under the guide groove, a printing control circuit, a power supply module, a second support, and a first support are further installed on the base plate, a heat sink fan is respectively fixed on the second support, the heat sink fan is tightly attached to an outer surface of the semiconductor laser, a stepper motor is disposed on the second support, a synchronization belt is connected to the stepper motor, the synchronization belt is connected to the ink jet cartridge, a belt pulley for driving the conveyor belt is provided at the conveyor belt, a first micro motor is connected to the belt pulley, a number of pushing blocks are disposed on the surface of the conveyor belt, and the first micro motor is mounted on the first support.

Further specifically, a sliding block is disposed at the elevation pushing plate, a linear guide rail is disposed in the sliding block, a driven bearing is disposed on the surface of the sliding block, a second slot photoelectric sensor used to detect the position of the sliding block is disposed on a side of the sliding block, a first slot photoelectric sensor is disposed on the other side of the sliding block, and a baffle is disposed on the sliding block.

Further specifically, a micro ball screw motor and a linear guide rail are disposed on the magazine holder, a nut is connected to the micro ball screw motor, and the nut is linked to the linear guide rail.

The present invention further discloses a printing method of the laser printer for pathological embedding cassettes in the foregoing technical solution. The method includes: transferring, by a host computer, a printing instruction to a printing control circuit; controlling, by the printing control circuit, a conveyor belt to move, so as to move an embedding cassette to a printing area; meanwhile, detecting, by a photoelectric sensor mounted in a moving direction of the conveyor belt, the position of the embedding cassette, transferring, by the photoelectric sensor, detected position information of the embedding cassette to the printing control circuit, and controlling, by the printing control circuit according to the information output by the photoelectric sensor, an ink jet cartridge to eject ink droplets to the embedding cassette; and subsequently, irradiate the ink droplets with a laser beam from a semiconductor laser, so that the ink droplets on the surface of the embedding cassette have a rapid increase in temperature and are cured, where after the temperature of the cured ink droplets reach a melting point of plastic, the ink droplets are melted on a surface layer of plastic and integrated well with plastic.

The beneficial effects of the present invention are as follows: 1. By ejecting pigment ink droplets on an embedding cassette and irradiating the ink droplets with a laser beam from a semiconductor laser, the ink droplets have a rapid increase in temperature and are cured, so that colors are applied on a plastic surface and can be easily recognized. 2. With a combination of a guide groove and a semilunar pushing wheel, the conveyance of the embedding cassettes is implemented effectively to facilitate an operator in picking up and placing the embedding cassettes. 3. The position of an embedding cassette can be directly precisely detected using a photoelectric sensor, so as to ensure the precise irradiation of the ink droplets by the semiconductor laser, thereby improving the curing quality.

Figure 1:
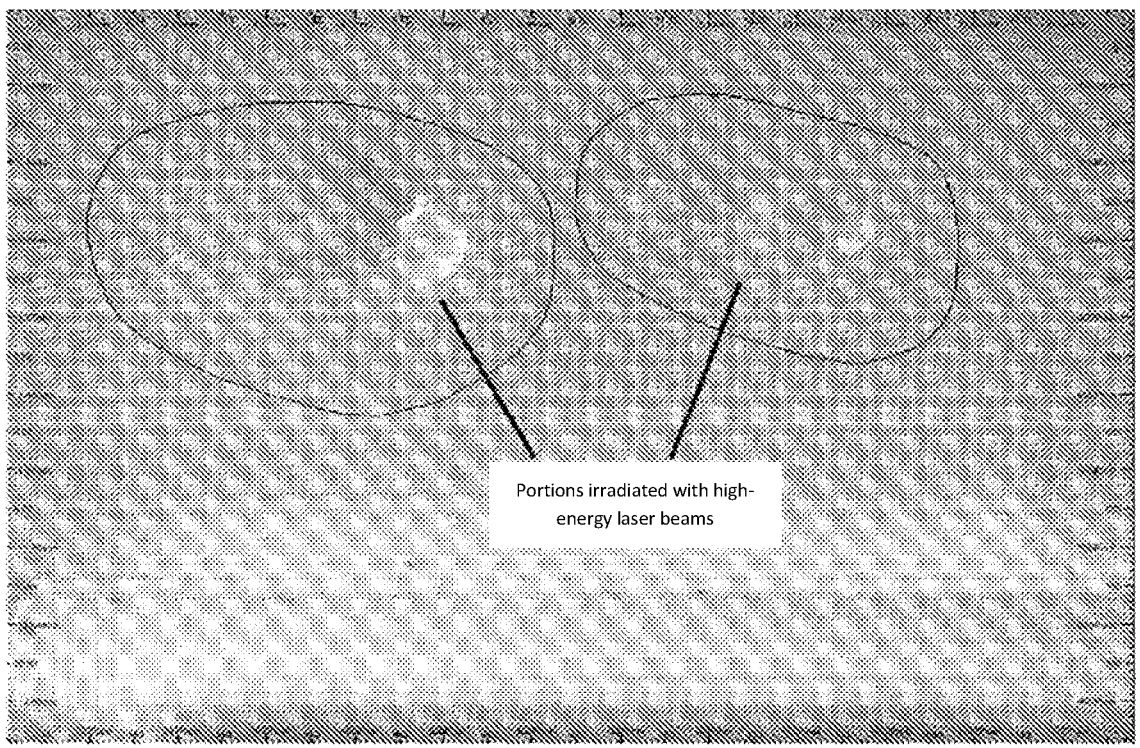
FIG. 1 is a diagram showing a result of irradiating a POM plastic surface with a laser beam.
Figure 2:
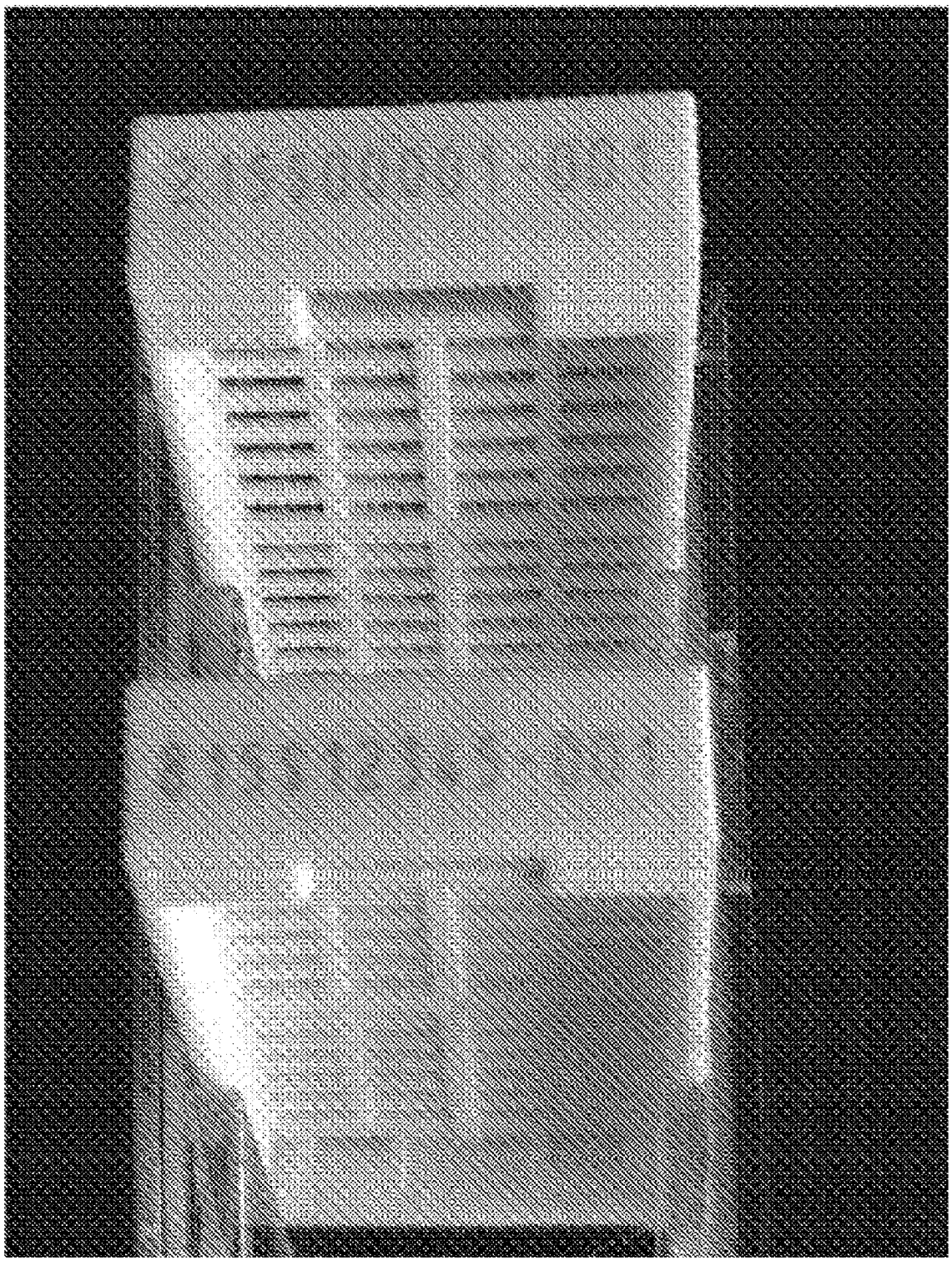
FIG. 2 is a diagram showing a real object of a printed POM pathological embedding cassette according to the present invention.
Figure 3:
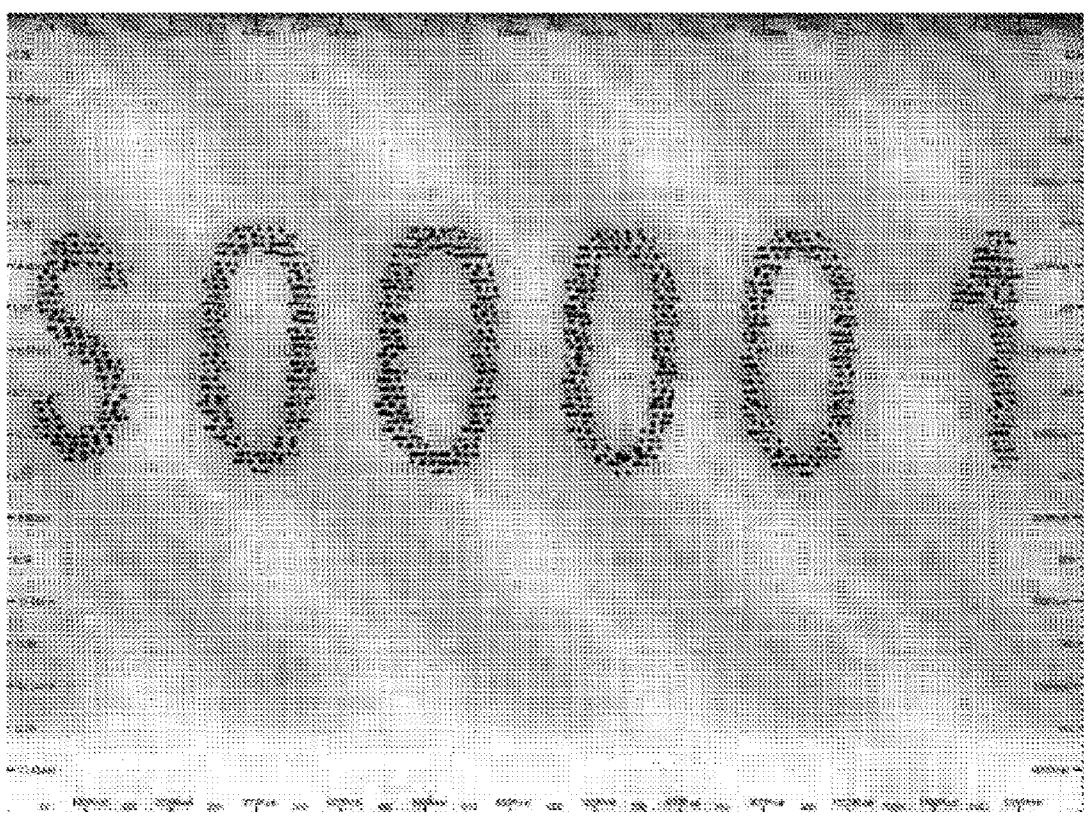
FIG. 3 is a partial enlarged view of a real object of a printed POM pathological embedding cassette according to the present invention.
Figure 4:
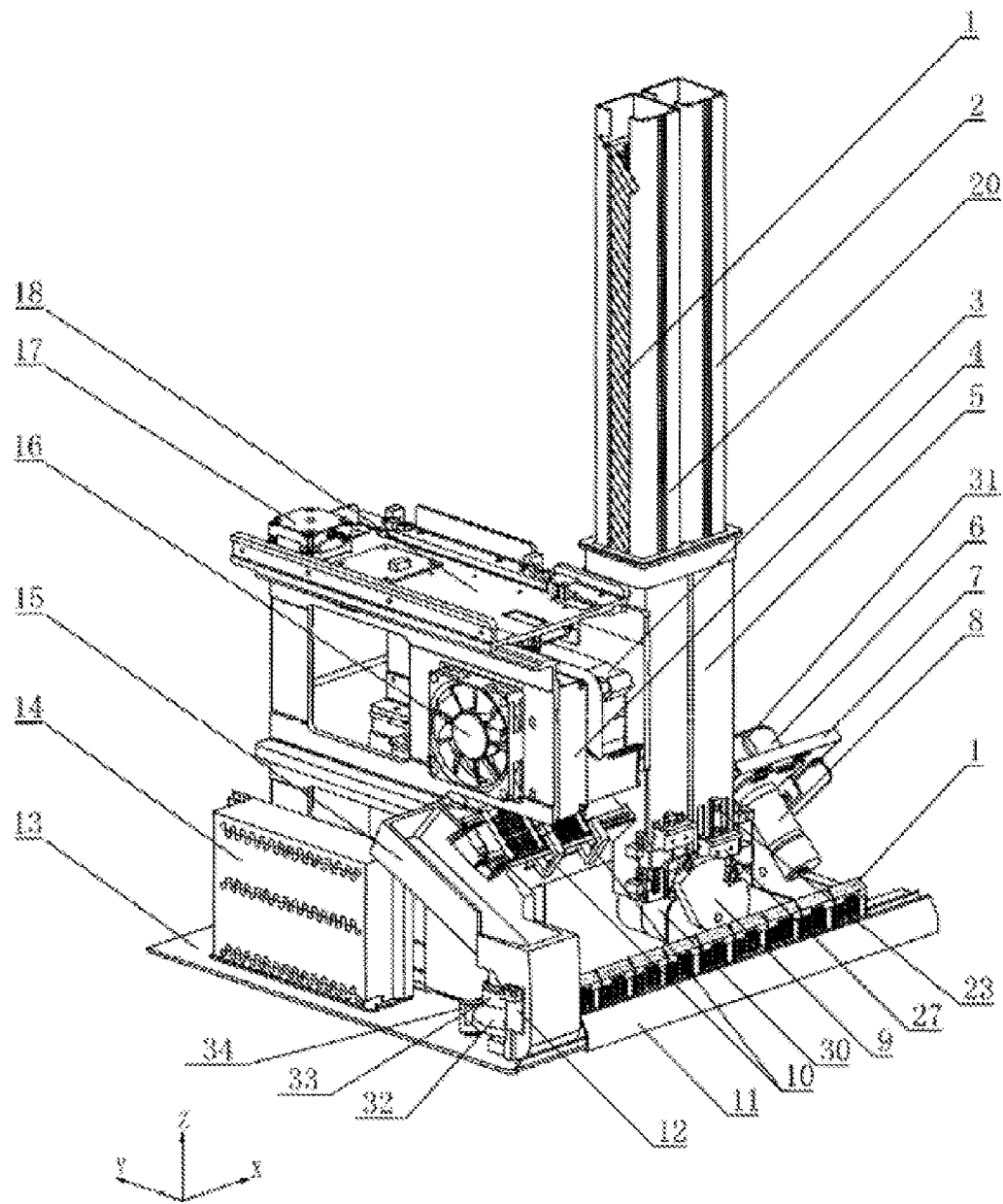
FIG. 4 is a schematic structural diagram according to the present invention.
Figure 5:
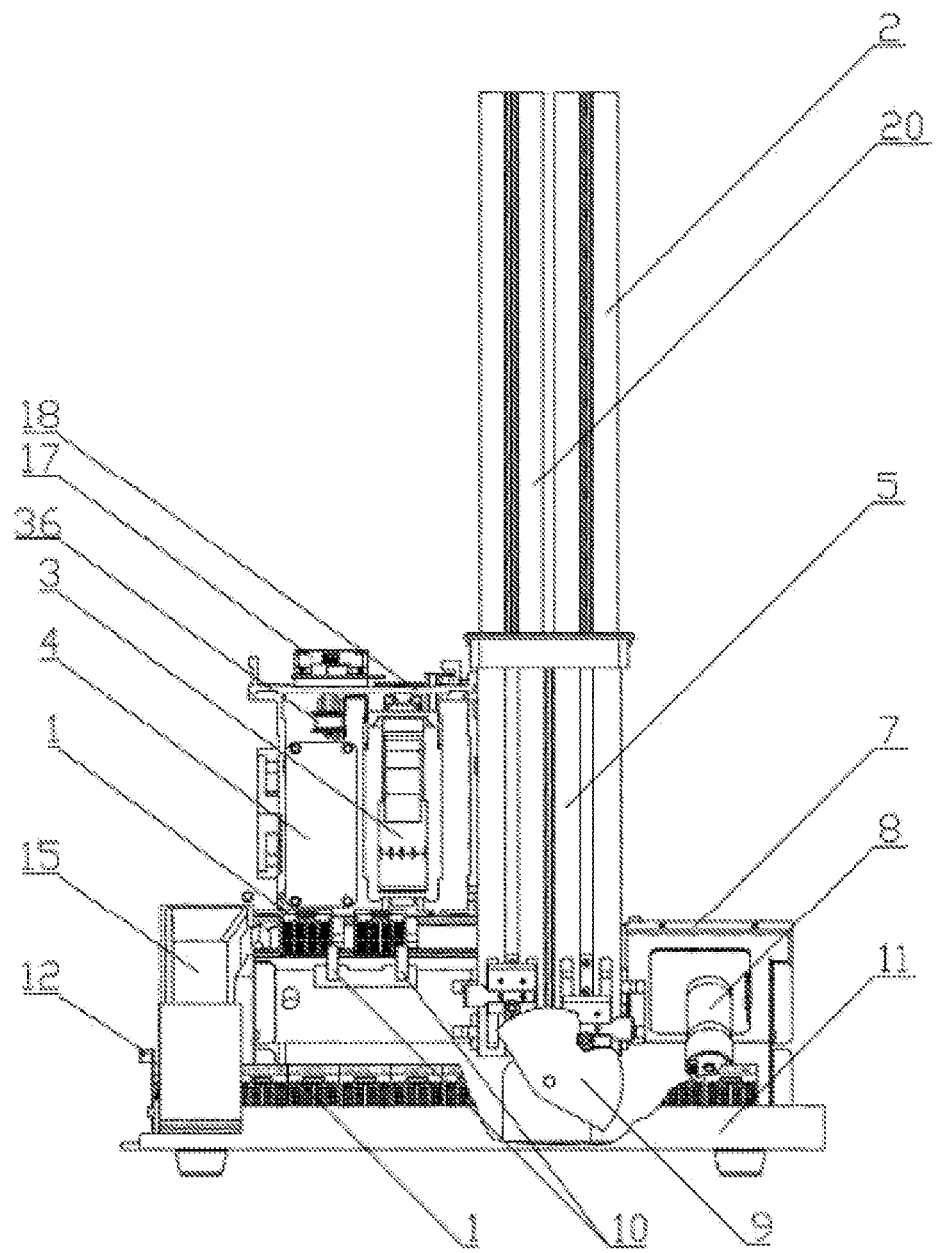
FIG. 5 is a schematic structural diagram at a first angle according to the present invention.
Figure 6:
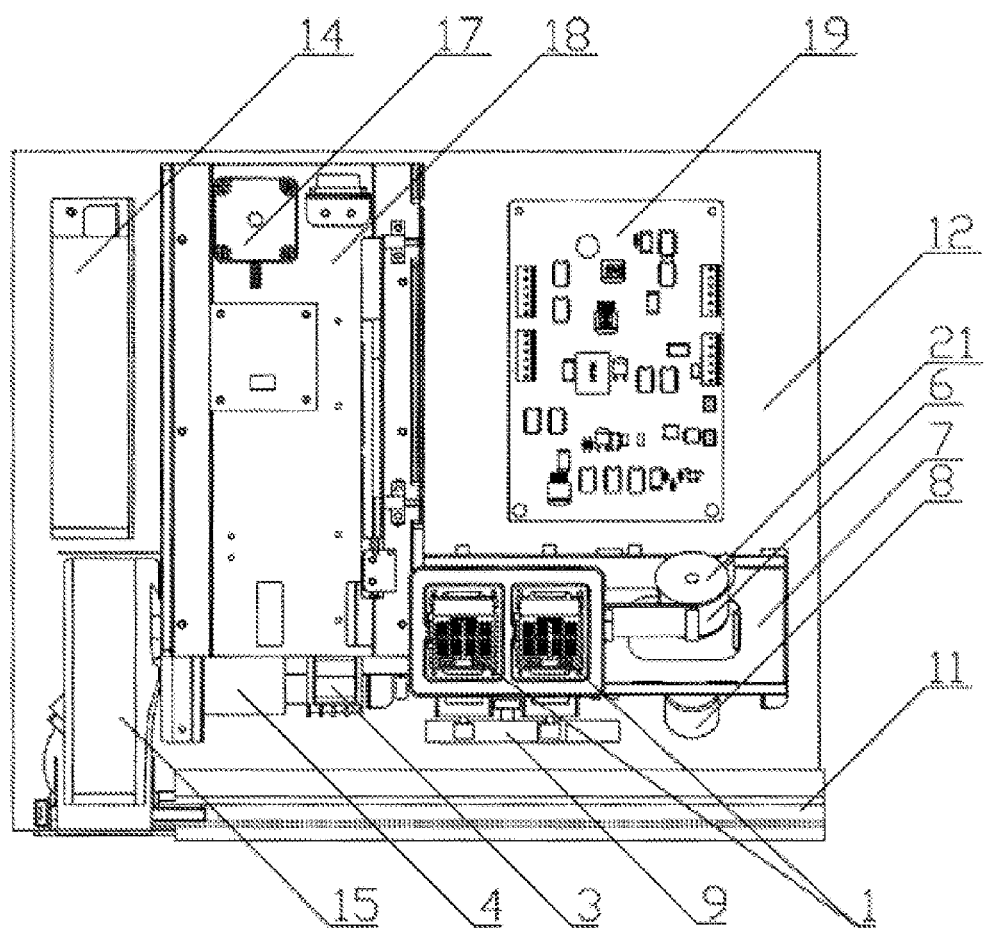
FIG. 6 is a schematic structural diagram of a top view according to the present invention.
Figure 7:
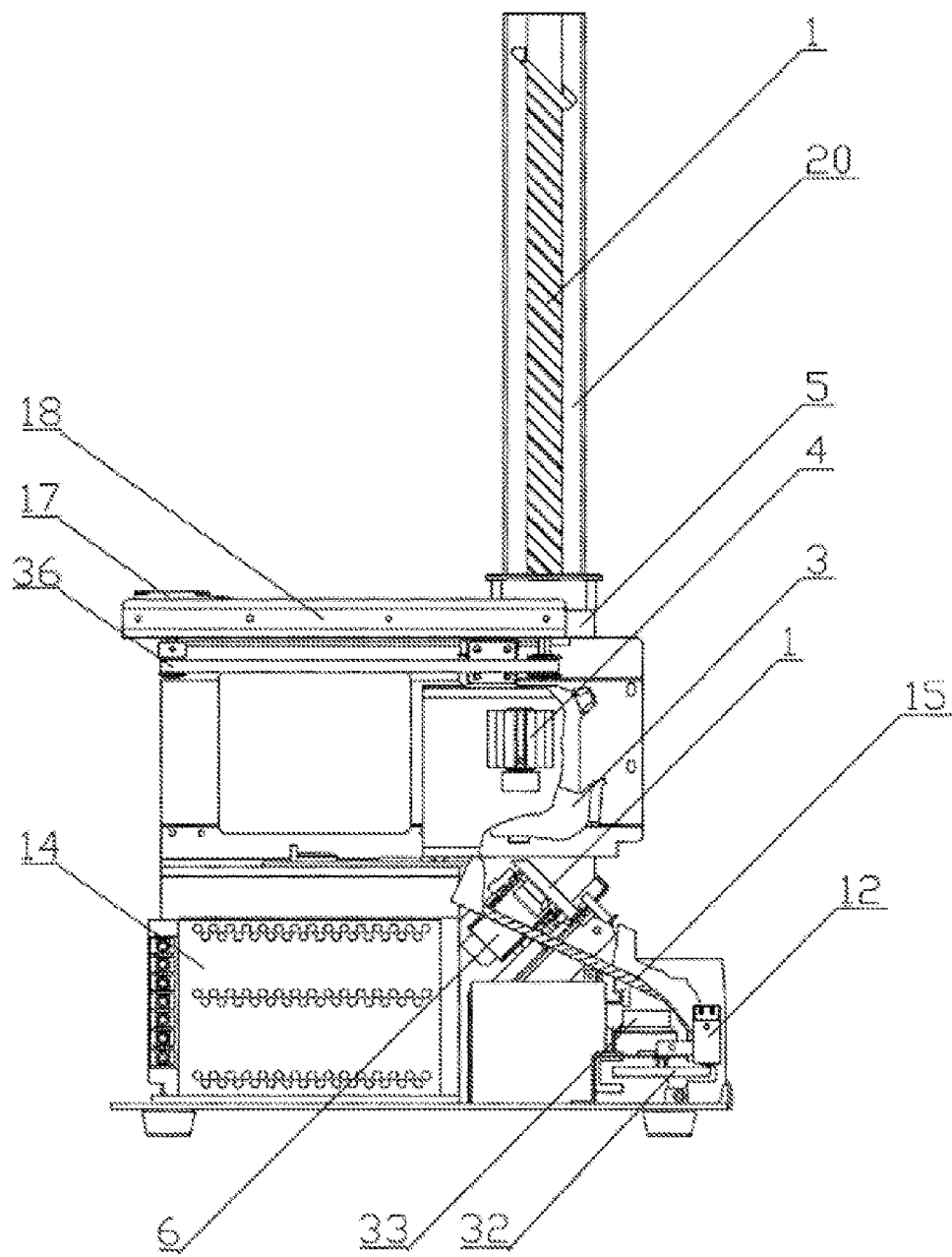
FIG. 7 is a schematic structural diagram at a second angle according to the present invention.

The numerals in the accompanying drawings are described as follows:

Embedding cassette 1; First magazine 2; Ink jet cartridge 3; Semiconductor laser 4; Magazine holder 5; Conveyor belt 6; First support 7; First micro motor 8; Cam 9; Photoelectric sensor 10; Guide groove 11; Reflective photoelectric sensor 12; Base plate 13; Power supply module 14; Slide 15; Heat sink fan 16; Stepper motor 17; Second support 18; Printing control circuit 19; Second magazine 20; Belt pulley 21; Left elevation pushing plate 22; Linear guide rail 23; Right elevation pushing plate 24; First slot photoelectric sensor 25; Second slot photoelectric sensor 26; Sliding block 27; Baffle 28; Driven bearing 29; Second micro motor 30; Pushing block 31; Semilunar pushing wheel 32; Third micro motor 33; Slot photoelectric sensor 34; Notch 35; Synchronization belt 36; Micro ball screw motor 37; Nut 38; Ball screw 39; and Photoelectric sensors 40.

DETAILED DESCRIPTION

The embodiment of the present invention is described below in detail. Examples of the embodiment are shown in the accompanying drawings. The same or similar numerals represent the same or similar elements or elements having the same or similar functions throughout the specification. The embodiment described below with reference to the accompanying drawings are exemplary, and are only used to explain the present invention but should not be construed as a limitation to the present invention.

A laser printer for pathological embedding cassettes and a printing method thereof according to the embodiment of the present invention are described below with reference to FIG. 1 to FIG. 21.

As shown in FIG. 1 to FIG. 21, the laser printer for pathological embedding cassettes described in the present invention includes an ink jet cartridge 3, where a conveyor belt 6 is disposed below the ink jet cartridge 3, a semiconductor laser 4 is disposed on a side of the ink jet cartridge 3, and a photoelectric sensor 10 for detecting the position of an embedding cassette 1 is disposed on the conveyor belt 6. A host computer transfers a printing instruction to a printing control circuit 19. The printing control circuit 19 controls the conveyor belt 6 to move, so as to move an embedding cassette 1 to a printing area. The ink jet cartridge 3 begins to eject ink droplets to the embedding cassette 1, and subsequently the semiconductor laser 4 emits a laser beam to irradiate the ink droplets, so that the ink droplets on the surface of the embedding cassette 1 have a rapid increase in temperature and are cured, where after the temperature of the cured ink droplets reach a melting point of plastic, the ink droplets are melted on a surface layer of plastic and integrated with plastic. In addition, the photoelectric sensor 10 directly precisely detects the position of the embedding cassette 1, to ensure that the semiconductor laser 4 can precisely irradiate the ink droplets, improving the curing quality of the ink droplets, so that the ink droplets can be thoroughly cured.

In addition, the laser printer for pathological embedding cassettes according to the present invention further has the following additional technical features, according to some embodiment of the present invention, and further specifically, a magazine holder 5 is disposed on the conveyor belt 6, the magazine holder 5 is located on a side of the ink jet cartridge 3, and the conveyor belt 6 passes through the magazine holder 5.

Further specifically, a first magazine 2 and a second magazine 20 are inserted at an upper portion of the magazine holder 5, and embedding cassettes 1 are respectively held in the first magazine 2 and the second magazine 20.

Further specifically, notches 35 are provided below the first magazine 2 and the second magazine 20, an elevation pushing plate is disposed at lowermost ends of the first magazine 2 and the second magazine 20, a cam 9 used to make the elevation pushing plate move up and down is disposed at a lower end portion of the elevation pushing plate, and a second micro motor 30 for driving the cam 9 to rotate is disposed at the cam 9.

Further specifically, the elevation pushing plate includes a left elevation pushing plate 22 and a right elevation pushing plate 24, top portions of the left elevation pushing plate 22 and the right elevation pushing plate 24 respectively support the first magazine 2 and the second magazine 20, two arc-shaped surfaces are disposed on the cam 9, and the arc-shaped surfaces are connected to each other.

Further specifically, a slide 15 is disposed on a side of the conveyor belt 6, a third micro motor 33 and a reflective photoelectric sensor 12 are disposed at a lower portion of the slide 15, a semilunar pushing wheel 32 is disposed on the third micro motor 33, a guide groove 11 is disposed on a side of the semilunar pushing wheel 32, and a slot photoelectric sensor 34 used to detect the angle of the semilunar pushing wheel 32 is disposed on a side of the semilunar pushing wheel 32.

Further specifically, a base plate 13 is disposed under the guide groove 11, the printing control circuit 19, a power supply module 14, a second support 18, and a first support 7 are further installed on the base plate 13, a heat sink fan 16 is respectively fixed on the second support 18, the heat sink fan is tightly attached to an outer surface of the semiconductor laser 4, a stepper motor 17 is disposed on the second support 18, a synchronization belt 36 is connected to the stepper motor 17, the synchronization belt 36 is connected to the ink jet cartridge 3, a belt pulley 21 for driving the conveyor belt 6 is disposed at the conveyor belt 6, a first micro motor 8 is equipped with the belt pulley 21, a number of pushing block 31 is disposed on the surface of the conveyor belt 6, and the first micro motor 8 is mounted on the first support 7.

Further specifically, a sliding block 27 is disposed at the elevation pushing plate, a linear guide rail 23 is disposed in the sliding block 27, a driven bearing 29 is disposed on the surface of the linear guide rail 23, a second slot photoelectric sensor 26 used to detect the position of the sliding block 27 is disposed on a side of the sliding block 27, a first slot photoelectric sensor 25 is provided on the other side of the sliding block 27, and a baffle 28 is disposed on the sliding block 27.

Figure 11:
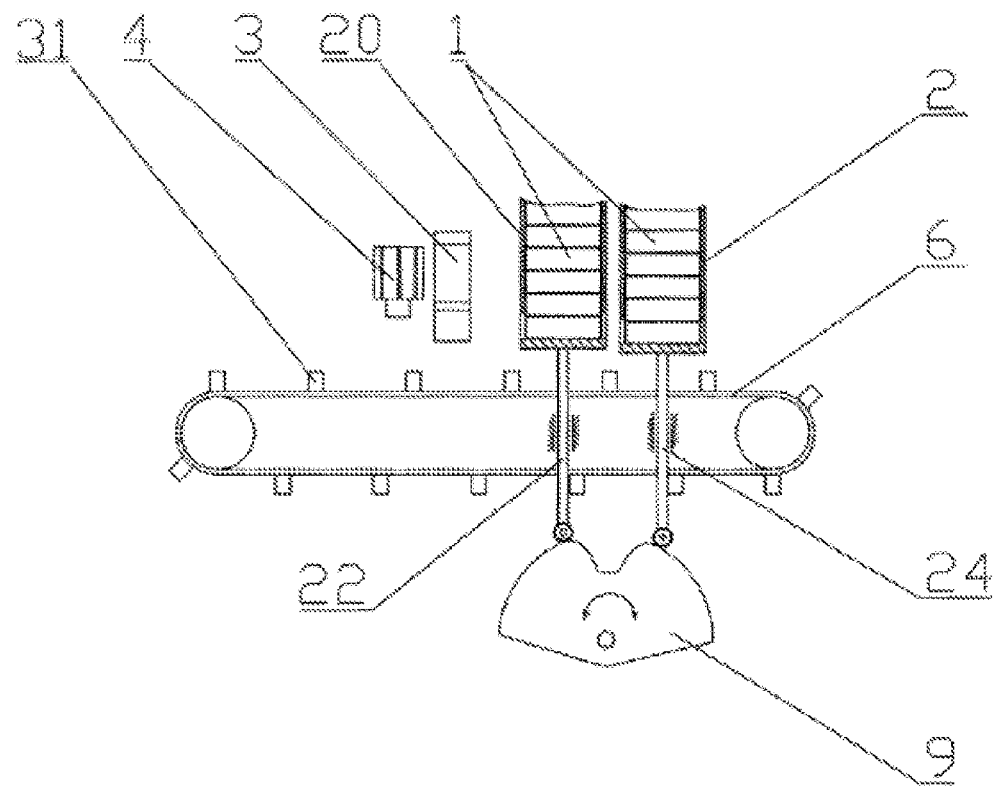
FIG. 11 to FIG. 16 are schematic structural diagrams of a use state of the present invention.

The working process of the structure:

As shown in FIG. 11, during standby: The cam 9 rotates to enable the left elevation pushing plate 22 and the right elevation pushing plate 24 to be in the positions of the highest points. The first magazine 2 and the second magazine 20 are respectively supported by the left elevation pushing plate 22 and the right elevation pushing plate 24, and are therefore also at the highest points. Embedding cassettes 1 are inside the magazines (not falling on the conveyor belt 6).

Figure 12:
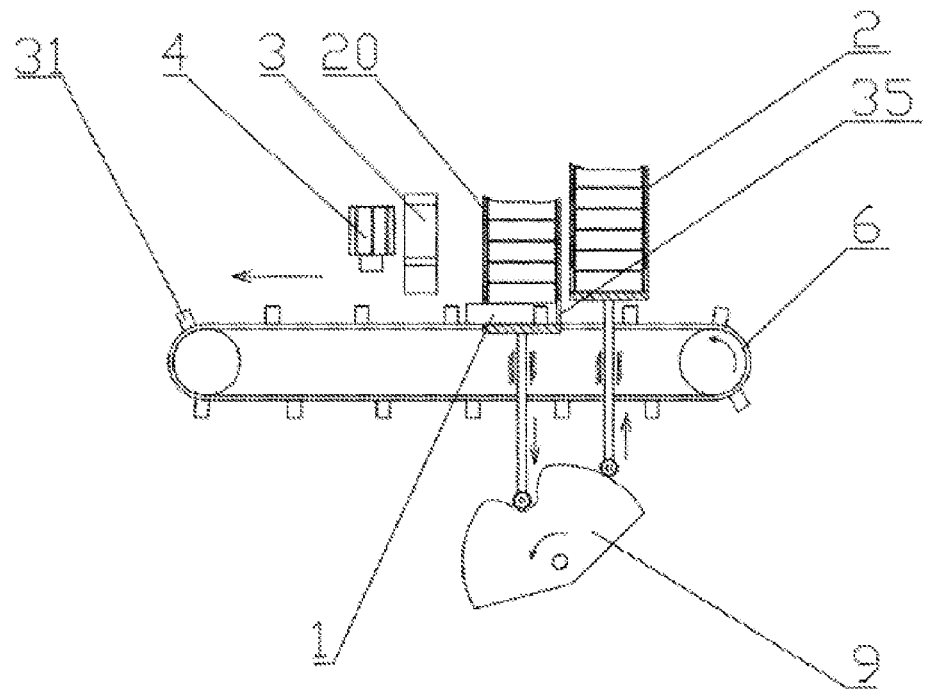
Figure 13:
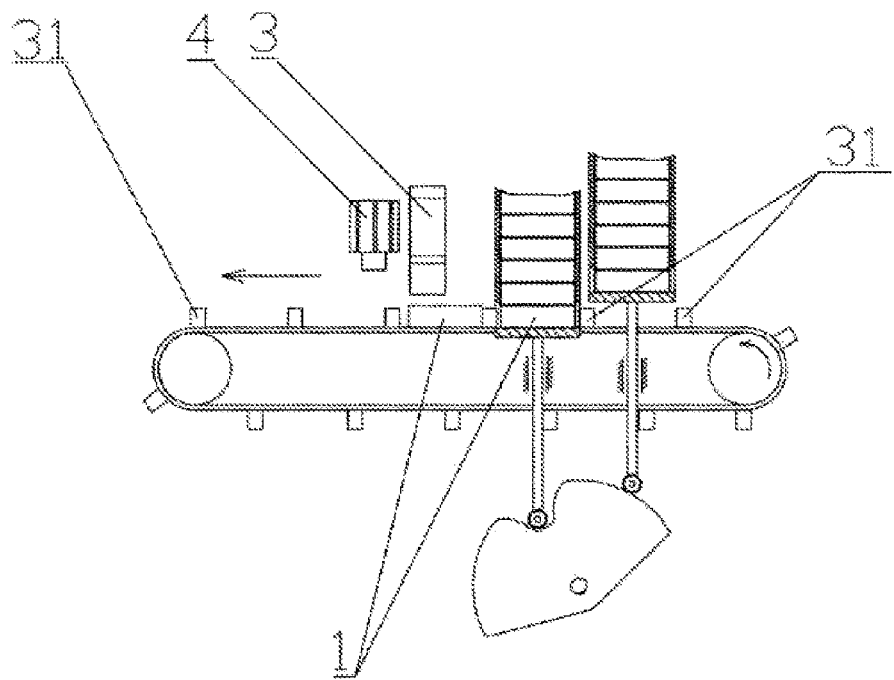
Figure 14:
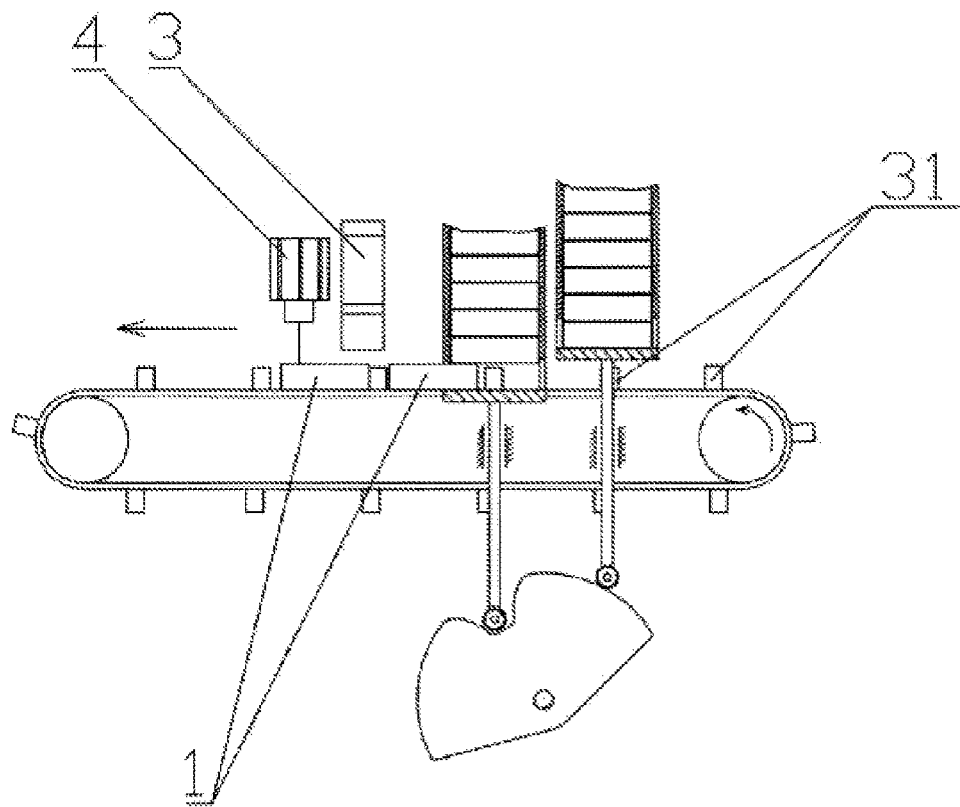
Figure 15:
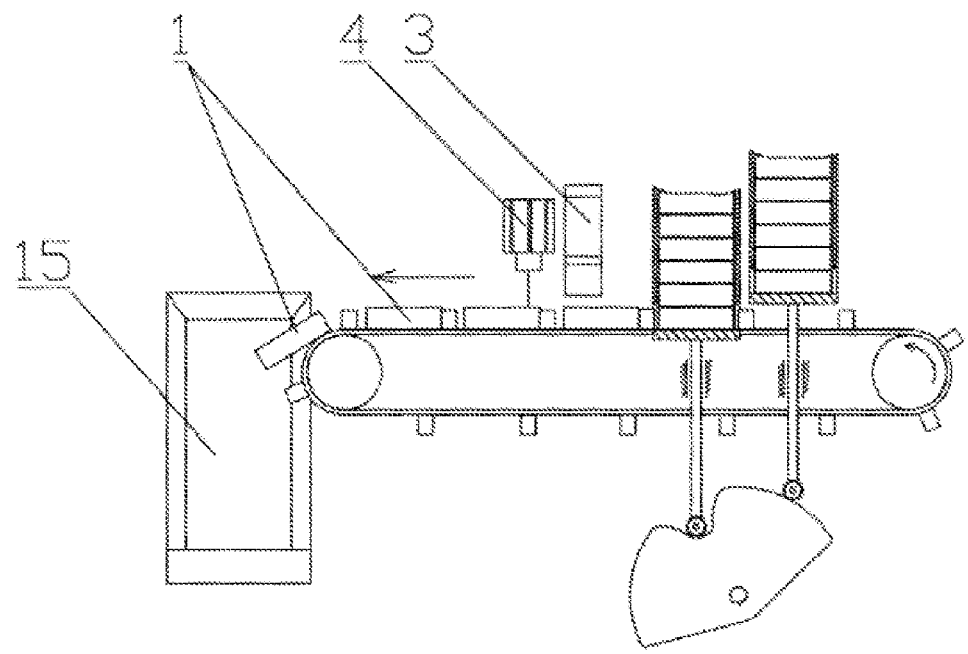
Figure 17:
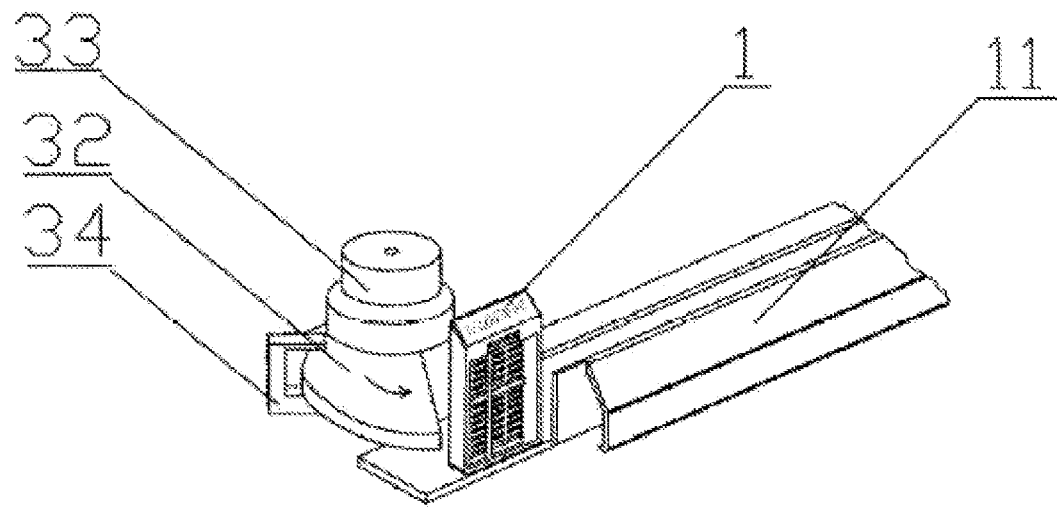
FIG. 17 to FIG. 20 are schematic structural diagrams of a working state of collecting embedding cassettes according to the present invention.
Figure 18:
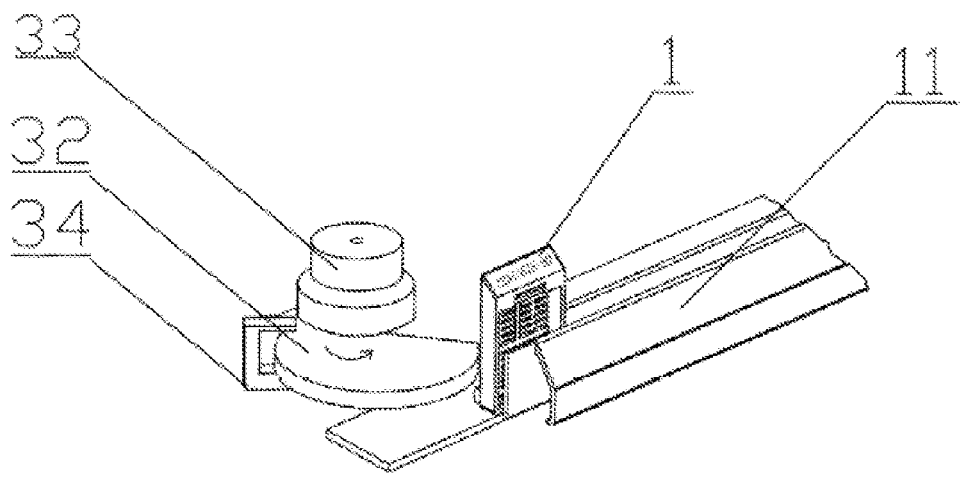
Figure 19:
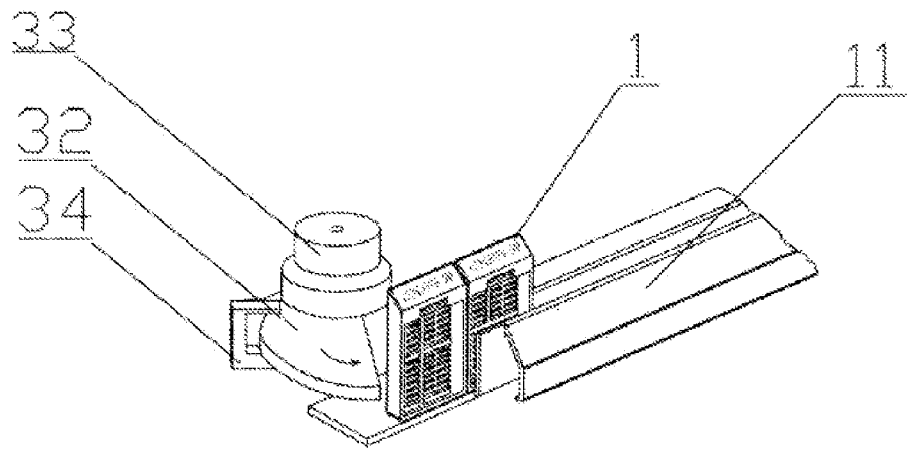
Figure 20:
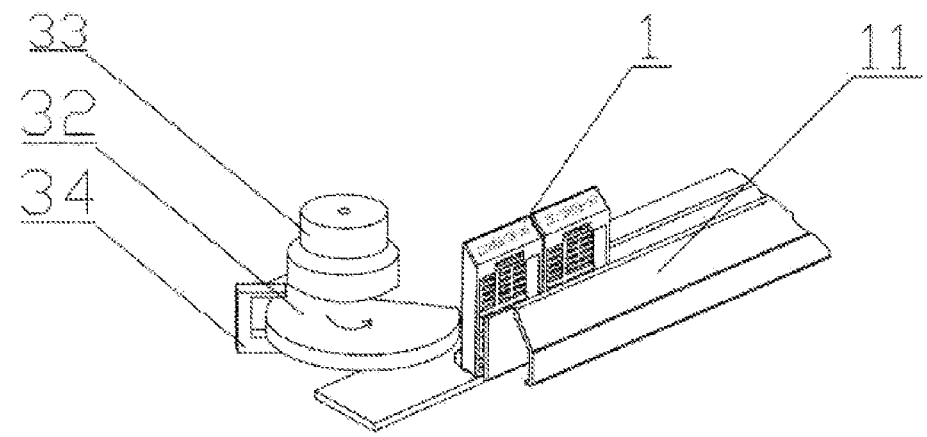

As shown in FIG. 12, in a printing state: The cam 9 rotates counterclockwise to a set angle. At this time, the first magazine 2 is still at a highest point, but the second magazine 20 moves downwardly to a lowest point. The conveyor belt 6 moves in a counterclockwise direction, and pushing blocks 31 fixed on the conveyor belt 6 at an equal interval move accordingly. When a pushing block 31 moves to the notch 35 below the second magazine 20, one lowermost embedding cassette 1 in the second magazine 20 is pushed out from the second magazine 20. As the conveyor belt 6 moves, the pushing block 31 conveys one embedding cassette 1 to a printing area of the ink jet cartridge 3. When the photoelectric sensor 10 detects that an embedding cassette 1 reaches a printing position of the ink jet cartridge 3, the printing control circuit 19 drives the ink jet cartridge 3 to print characters on a labeling surface of the embedding cassette 1, and at the same time a pushing block 31 prepares to push out a next embedding cassette 1, as shown in FIG. 13. The conveyor belt 6 continues to move. The ink jet cartridge 3 completes printing of characters on one embedding cassette 1. The imprinted embedding cassette 1 is immediately conveyed below the semiconductor laser 4. The photoelectric sensor 10 detects that the embedding cassette 1 reaches an irradiation position of the semiconductor laser 4, the printing control circuit 19 drives the semiconductor laser 4 to emit a high-energy laser beam to irradiate the characters on the embedding cassette 1. Water molecules in ink droplet are rapidly evaporated by the high-energy laser beam and then the pigment of ink and the surface of the embedding cassette 1 melt together, as shown in FIG. 14. The foregoing process continues. The pushing block 31 moves the embedding cassette 1 that has undergone laser irradiation to an end of the conveyor belt 6. The embedding cassette 1 turns and falls in the track of the slide 15, as shown in FIG. 15. The embedding cassette 1 slides along the track of the slide 15 down to the bottom of the slide 15. The reflective photoelectric sensor 12 detects that the embedding cassette 1 falls in. The printing control circuit 19 drives the third micro motor 33 to drive the semilunar pushing wheel 32 to rotate in an arrow direction in the figure, as shown in FIG. 17. As the semilunar pushing wheel 32 rotates, the embedding cassette 1 is pushed into the guide groove 11, as shown in FIG. 18. If an embedding cassette 1 subsequently slides down to the bottom of the slide 15, the semilunar pushing wheel 32 continues to rotate and pushes the embedding cassette 1 that subsequently reaches the bottom of the slide 15 into the guide groove 11, as shown in FIG. 19 and FIG. 20. The foregoing process is repeated, so that embedding cassettes 1 can be neatly arranged in the guide groove 11, facilitating the retrieval and use by operator.

Figure 21:
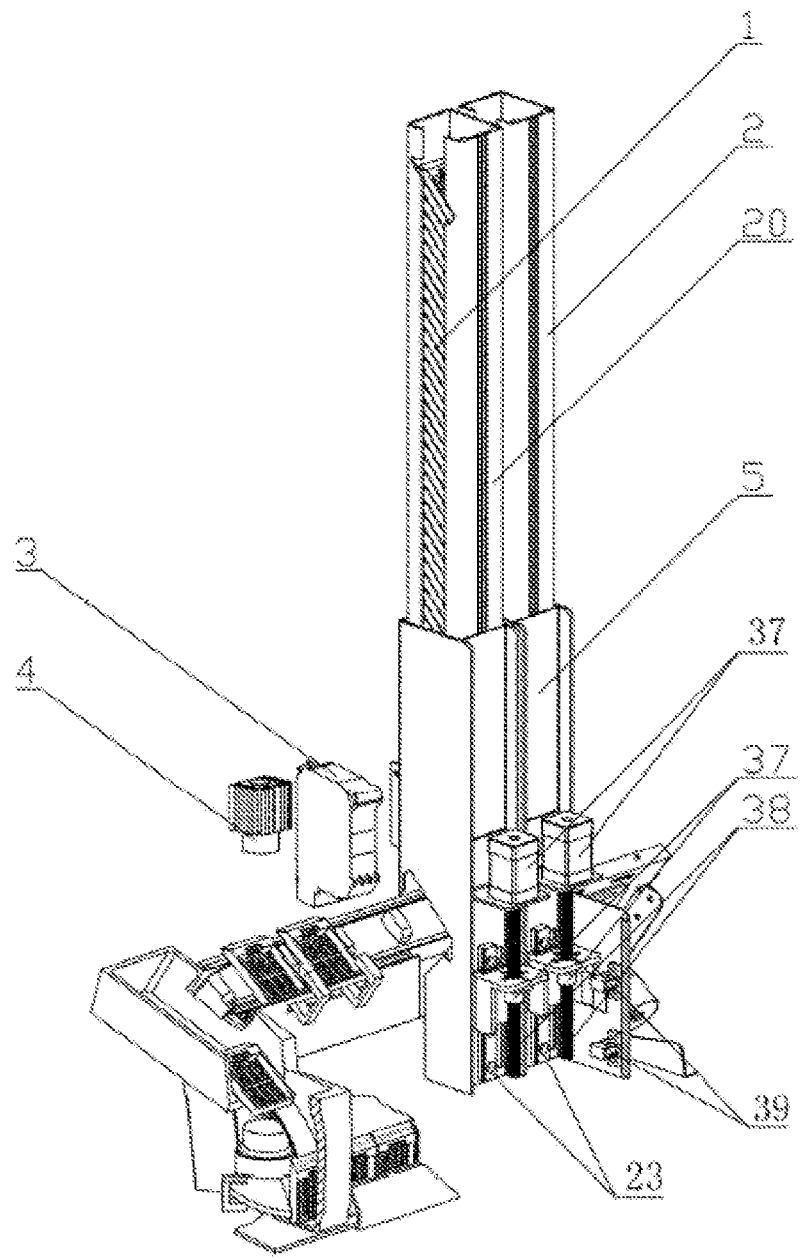
FIG. 21 is a schematic structural diagram of another embodiment of the present invention.

Further specifically, a micro ball screw motor 37 and a linear guide rail 23 are disposed on the magazine holder 5, a nut 38 is connected to the micro ball screw motor 37, and the nut 38 is linked to the linear guide rail 23. As shown in FIG. 21, the micro ball screw motor 37 and the linear guide rail 23 are mounted in this embodiment. The left elevation pushing plate 22 and the right elevation pushing plate 24 are respectively mounted on sliding blocks of two linear guide rails 23. The nut 38 is linked to the linear guide rail 23. When the micro ball screw motor 37 drives a ball screw 39 to rotate clockwise or counterclockwise, the left elevation pushing plate 22 and the right elevation pushing plate 24 can move reciprocally in a Z-axis direction of the linear guide rail 23, so that the second magazine 20 and the first magazine 2 supported by the left elevation pushing plate 22 and the right elevation pushing plate 24 also move up and down reciprocally. The first slot photoelectric sensor 25 is further mounted on an embedding cassette loading mechanism in this embodiment, and used to detect the position of the nut 38. The first slot photoelectric sensor 25 sends a signal of detection to the control circuit 19. The output logic of the control circuit 19 may drive the micro ball screw motor 37, to implement automatic switching of the first magazine 2 and the second magazine 20 and automatic loading of an embedding cassette. If a plurality of embedding cassette loading mechanisms in this embodiment is mounted on the printer, more magazines can be controlled at the same time, so as to adapt to the requirements of batch printing of pathological embedding cassettes in pathological laboratories of hospitals.

Figure 16:
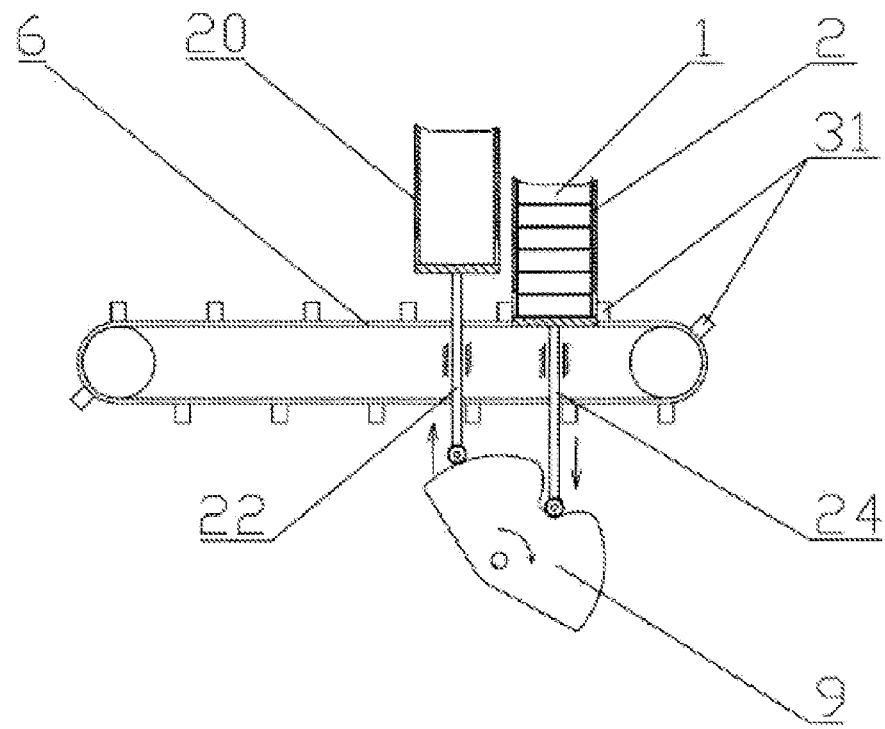

Magazines are automatically shifted. The first magazine 2 and the second magazine 20 are disposed in the printer. If embedding cassettes in the first magazine 2 or the second magazine 20 is empty, the empty magazine will be shifted. Therefore, the printing is continuous during the magazine replacement. As shown in FIG. 16, the cam 9 rotates clockwise to a particular angle elevating empty magazine 20 to a highest point. Meanwhile the first magazine 2 filled with embedding cassettes 1 is move down to a lowest point. A pushing block 31 in moving then pushes an embedding cassette 1 out from the first magazine 2 and transports the embedding cassette 1 to the printing area, thus ensuring a continuous printing flow.

The present invention further discloses a printing method of the laser printer for pathological embedding cassettes. The method includes: transferring, by a host computer, a printing instruction to a printing control circuit 19; controlling, by the printing control circuit 19, a conveyor belt 6 to move, so as to move an embedding cassette 1 to a printing area; meanwhile, detecting, by a photoelectric sensor 10 mounted in a moving direction of the conveyor belt, the position of the embedding cassette 1, transferring, by the photoelectric sensor 10, detected position information of the embedding cassette 1 to the printing control circuit 19, and controlling, by the printing control circuit 19 according to the signals from the photoelectric sensor 10, an ink jet cartridge 3 to eject ink droplets to the embedding cassette 1; and subsequently, irradiating, by a semiconductor laser 4, the ink droplets with a laser beam, so that the ink droplets on the surface of the embedding cassette 1 have a rapid increase in temperature and are cured, where after the temperature of the cured ink droplets reach a melting point of plastic, the ink droplets are melted on a surface layer of plastic and integrated with plastic. The ink jet cartridge 3 and the semiconductor laser 4 are mounted on the second support 18 and are linearly arranged along an X axis. The semiconductor laser 4 is driven by the control circuit 19. When the embedding cassette 1 moves right below the semiconductor laser 4, the semiconductor laser 4 emits a high-energy laser beam. A heat sink fan 16 is further assembled on the semiconductor laser 4. A stepper motor 17 is mounted on the second support 18. The stepper motor 17 is drives the ink jet cartridge 3 via a synchronization belt 36, so that the ink jet cartridge 3 can move reciprocally in a Y-axis direction. The ink jet cartridge 3 is driven by the printing control circuit 19, and can print characters on an embedding cassette 1 that moves below the ink jet cartridge 3. In addition, the embedding cassette 1 is continuously supplied for printing. The photoelectric sensor 10 is used to directly detect the position of each embedding cassette 1, signals and data is updated in time, and the implementation of precise printing is facilitated.

Figure 8:
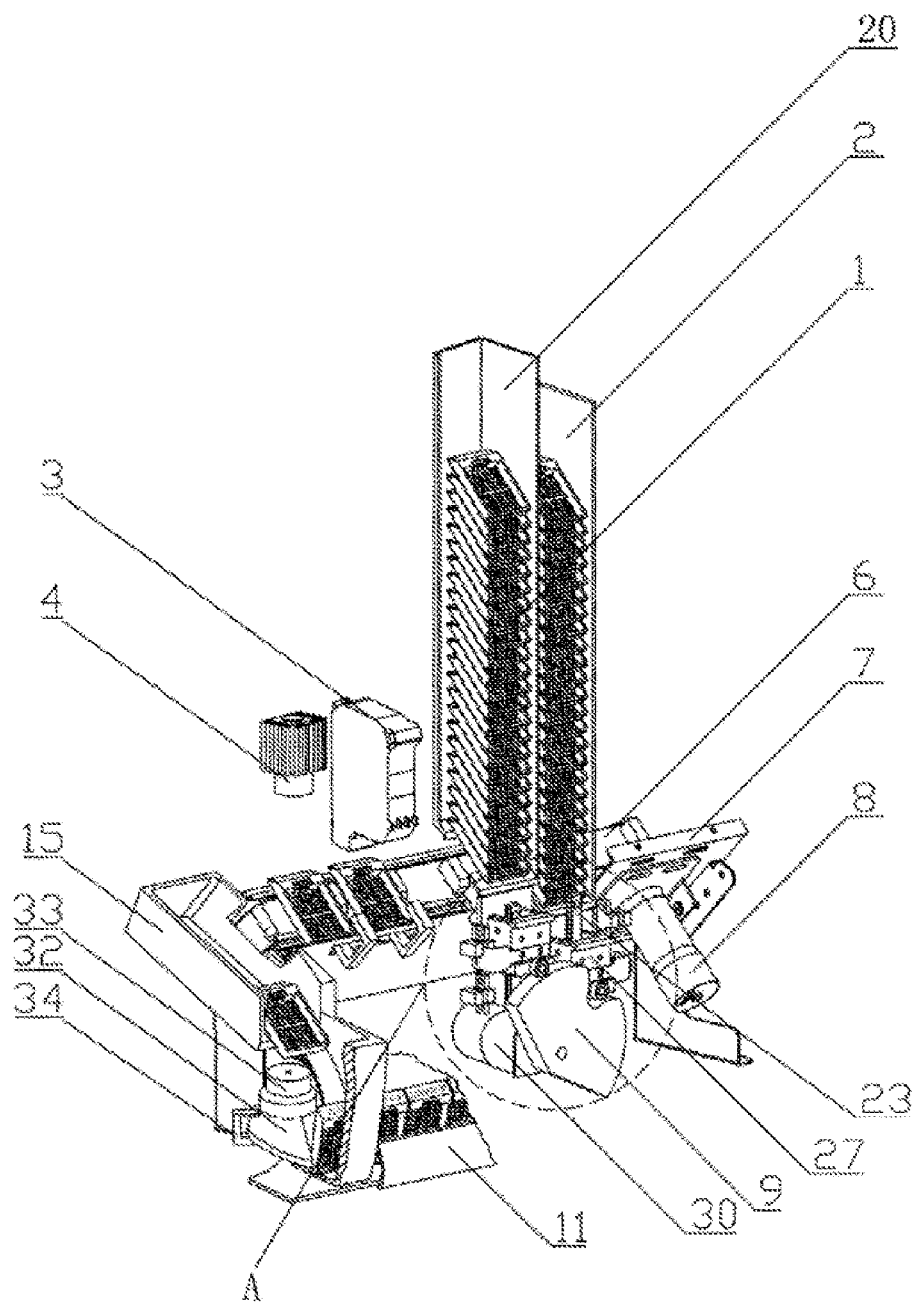
FIG. 8 is a schematic structural diagram at a third angle according to the present invention.
Figure 10:
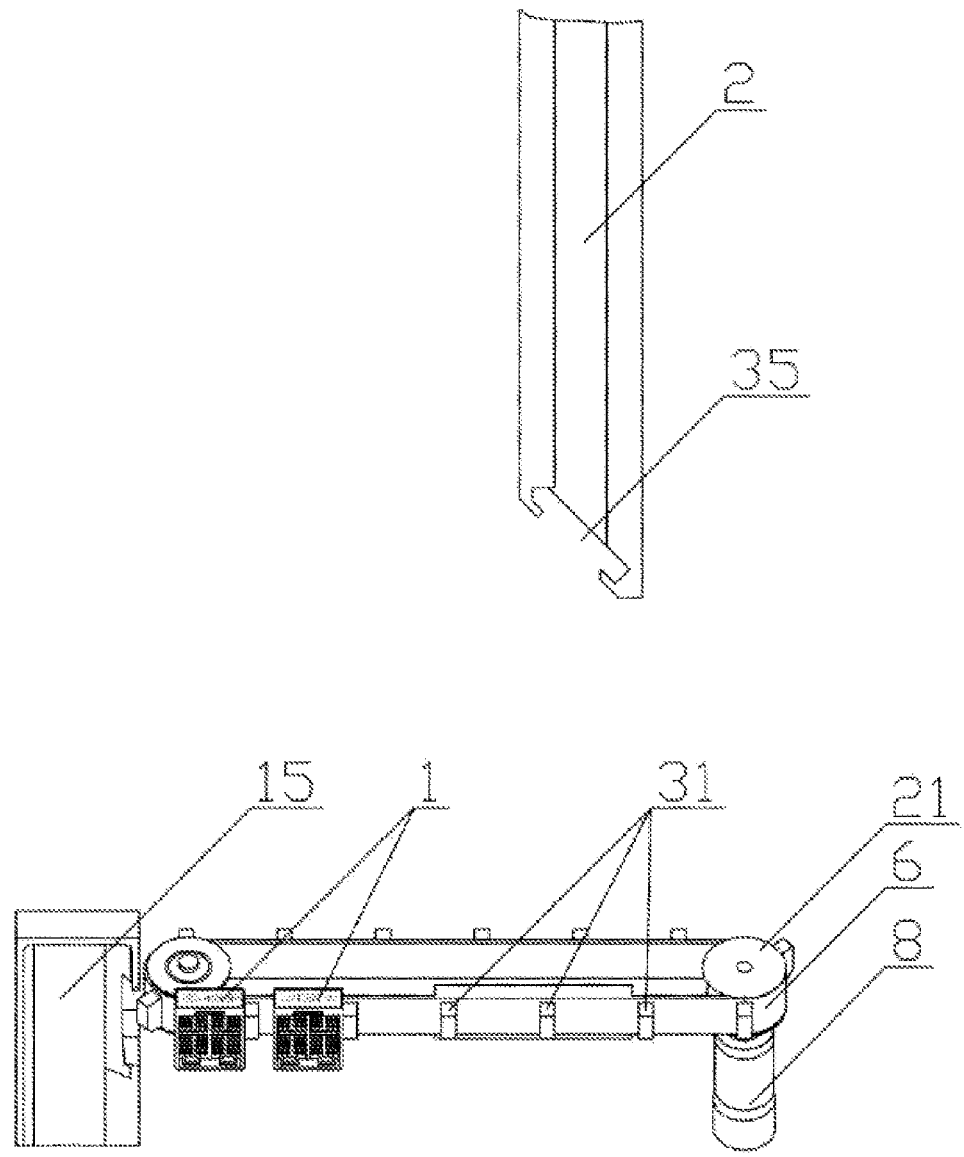
FIG. 10 is a schematic structural diagram of a magazine, a belt pulley, a first micro motor, a conveyor belt, an embedding cassette, and a slide being connected.

An embedding cassette conveyor mechanism includes a support 7, the conveyor belt 6, a micro motor 8, a belt pulley 21, and the like. Pushing blocks 31 are mounted at an equal distance on the conveyor belt 6. The conveyor belt 6 is driven by the micro motor 8 and the belt pulley 21 to move counterclockwise, as shown in FIG. 8 and FIG. 10. The micro motor 8, the belt pulley 21, and the conveyor belt 6 are mounted on the support 7. The support 7 is specially designed so that the conveyor belt 6 has a 45° inclination after being mounted on the support 7. Because a labeling surface of a pathological embedding cassette is usually 45°, the conveyor belt 6 mounted with a 45° inclination can make a labeling surface of an embedding cassette 1 conveyed on the conveyor belt 6 to be at 0°, so that the perpendicularly mounted ink jet cartridge 3 can easily print characters on the labeling surface of the embedding cassette. The photoelectric sensor 10 used to detect the movement position of the embedding cassette is further mounted on the embedding cassette conveyor mechanism.

Figure 9:
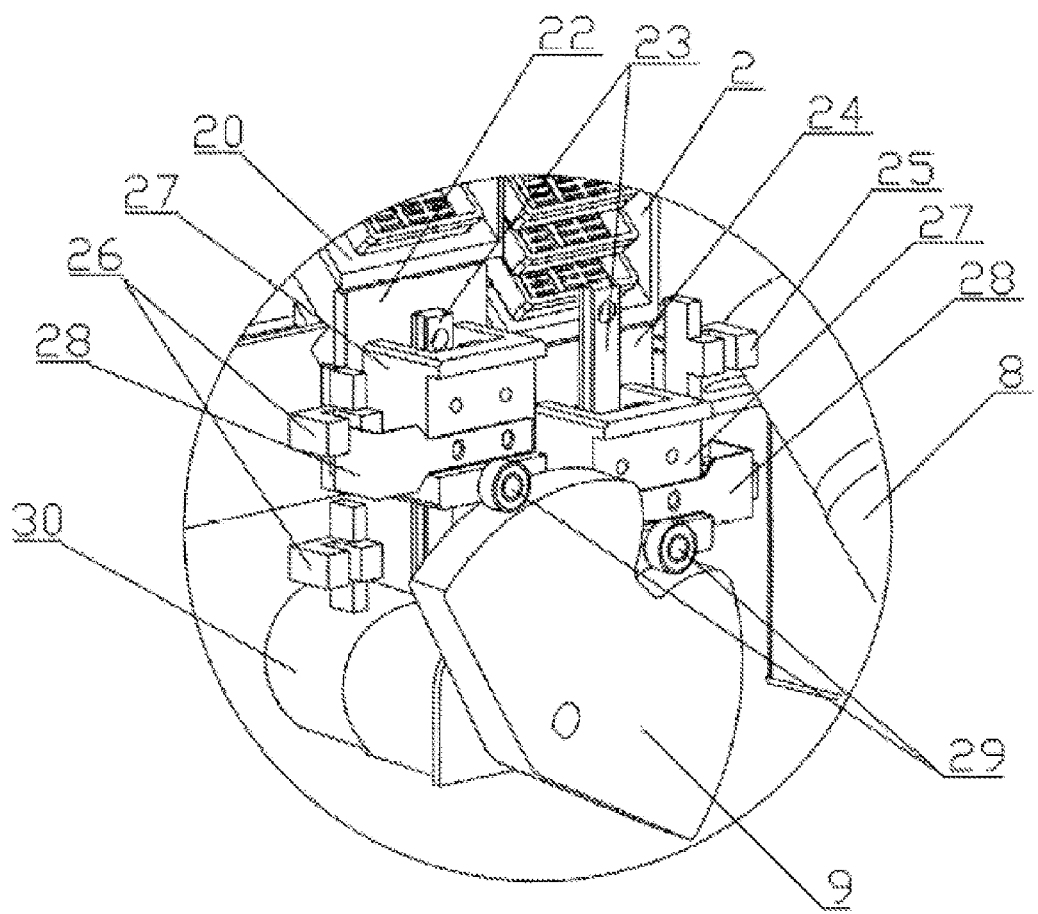
FIG. 9 is a schematic structural diagram of a position A in FIG. 8 being partially enlarged.

An embedding cassette loading mechanism includes a first magazine 2, a second magazine 20, a magazine holder 5, a cam 9, a micro motor 30, and the like, as shown in FIG. 8 and FIG. 9. The embedding cassette loading mechanism spans above the conveyor belt 6. The first magazine 2 and the second magazine 20 are respectively filled with several embedding cassettes 1. The bottoms of the first magazine 2 and the second magazine 20 are at 45° and notches 35 are opened on two sides, as shown in FIG. 10. The embedding cassettes 1 are stacked at 45° in the first magazine 2 and the second magazine 20. A lowermost embedding cassette 1 can be moved out from the notches 35. The first magazine 2 and the second magazine 20 are respectively inserted in the magazine holder 5 and can move reciprocally in a Z-axis direction in the magazine holder 5. Two linear guide rails 23 and two sliding blocks 27 are mounted on the magazine holder 5. A left elevation pushing plate 22 and a right elevation pushing plate 24 are respectively fixed on the two sliding blocks 27. The left elevation pushing plate 22 supports the bottom of the magazine 20, and the right elevation pushing plate 24 supports the bottom of the magazine 2. A driven bearing 29 is further respectively mounted on the two sliding blocks 27. The micro motor 30 is linked to the cam 9. The micro motor 30 rotates in a clockwise or counterclockwise direction by a particular rotation angle, the cam 9 rotates accordingly. The driven bearing 29 drives the sliding blocks 27 to move reciprocally in the Z-axis direction, so that the left elevation pushing plate 22 and the right elevation pushing plate 24 as well as the first magazine 2 and the second magazine 20 supported by the left elevation pushing plate 22 and the right elevation pushing plate 24 move up and down accordingly. A first slot photoelectric sensor 25 and a second slot photoelectric sensor 26 are further mounted on the magazine holder 5. A baffle 28 is mounted on the sliding block 27. The baffle 28 moves along with the sliding blocks 27, and is used to detect the movement position of the sliding blocks 27.

An embedding cassette collecting mechanism includes a slide 15, a third micro motor 33, a semilunar pushing wheel 32, a guide groove 11, and the like. The slide 15 is mounted at an end of the conveyor belt 6. The third micro motor 33 is linked to the semilunar pushing wheel 32 and is mounted below the slide 15. When the semilunar pushing wheel 32 rotates, the embedding cassette 1 that falls below the slide 15 may be transferred from the slide 15 and enter the guide groove 11. A reflective photoelectric sensor 12 and a slot photoelectric sensor 34 are further mounted on the embedding cassette collecting mechanism. The reflective photoelectric sensor 12 is used to detect whether an embedding cassette 1 falls below the slide 15. The slot photoelectric sensor 34 is used to detect the rotation position of the semilunar pushing wheel 32.

The above-mentioned contents are a merely preferred embodiment of the present invention, and are not used to limit the present invention, and wherever within the spirit and principle of the present invention, any modifications, equivalent replacements, improvements etc., shall be all contained within the scope of protection of the present invention.

What is claimed is:

1. A laser printer for pathological embedding cassettes, comprising an ink jet cartridge (3) filled with pigment ink, wherein a conveyor belt (6) is disposed below the ink jet cartridge (3), a semiconductor laser (4) is disposed on a side of the ink jet cartridge (3), and a photoelectric sensor (10) for detecting the position of an embedding cassette (1) is disposed in a moving direction of the conveyor belt (6);

wherein a magazine holder (5) is disposed on the conveyor belt (6), the magazine holder (5) is located on a side of the ink jet cartridge (3), and the conveyor belt (6) passes through the magazine holder (5);

wherein a first magazine (2) and a second magazine (20) are inserted at an upper portion of the magazine holder (5), and embedding cassettes (1) are respectively held in the first magazine (2) and the second magazine (20);

wherein notches (35) are provided below the first magazine (2) and the second magazine (20), an elevation pushing plate is disposed at lowermost ends of the first magazine (2) and the second magazine (20), a cam (9) used to make the elevation pushing plate move up and down is disposed at a lower end portion of the elevation pushing plate, and a second micro motor (30) for driving the cam (9) to rotate is disposed at the cam (9).

2. The laser printer for pathological embedding cassettes according to claim 1, wherein the elevation pushing plate comprises a left elevation pushing plate (22) and a right elevation pushing plate (24), top portions of the left elevation pushing plate (22) and the right elevation pushing plate (24) respectively support the first magazine (2) and the second magazine (20), two arc-shaped surfaces are disposed on the cam (9), and the arc-shaped surfaces are connected to each other.

3. A printing method of the laser printer for pathological embedding cassettes according to claim 2, wherein the method comprises: transferring, by a host computer, a printing instruction to a printing control circuit (19); controlling, by the printing control circuit (19), a conveyor belt (6) to move, so as to move an embedding cassette (1) to a printing area; meanwhile, detecting, by a photoelectric sensor (10), the position of the embedding cassette (1), transferring, by the photoelectric sensor (10), detected position information of the embedding cassette (1) to the printing control circuit (19), and driving, by the printing control circuit (19) according to the information output by the photoelectric sensor (10), an ink jet cartridge (3) to eject ink droplets to the embedding cassette (1); and subsequently, driving, by the printing control circuit (19), a semiconductor laser (4) to irradiate the ink droplets with a laser beam, so that the ink droplets on the surface of the embedding cassette (1) have a rapid increase in temperature and are cured, wherein after the temperature of the cured ink droplets reach a melting point of plastic, the ink droplets are melted on a surface layer of plastic and integrated with plastic.

4. The laser printer for pathological embedding cassettes according to claim 1, wherein a sliding block (27) is disposed at the elevation pushing plate, a linear guide rail (23) is disposed in the sliding block (27), a driven bearing (29) is disposed on the surface of the sliding block (27), a second slot photoelectric sensor (26) used to detect the position of the sliding block (27) is disposed on a side of the sliding block (27), a first slot photoelectric sensor (25) is disposed on the other side of the sliding block (27), and a baffle (28) is disposed on the sliding block (27).

5. A printing method of the laser printer for pathological embedding cassettes according to claim 4, wherein the method comprises: transferring, by a host computer, a printing instruction to a printing control circuit (19); controlling, by the printing control circuit (19), a conveyor belt (6) to move, so as to move an embedding cassette (1) to a printing area; meanwhile, detecting, by a photoelectric sensor (10), the position of the embedding cassette (1), transferring, by the photoelectric sensor (10), detected position information of the embedding cassette (1) to the printing control circuit (19), and driving, by the printing control circuit (19) according to the information output by the photoelectric sensor (10), an ink jet cartridge (3) to eject ink droplets to the embedding cassette (1); and subsequently, driving, by the printing control circuit (19), a semiconductor laser (4) to irradiate the ink droplets with a laser beam, so that the ink droplets on the surface of the embedding cassette (1) have a rapid increase in temperature and are cured, wherein after the temperature of the cured ink droplets reach a melting point of plastic, the ink droplets are melted on a surface layer of plastic and integrated with plastic.

6. The laser printer for pathological embedding cassettes according to claim 1, wherein a micro ball screw motor (37) and a linear guide rail (23) are disposed on the magazine holder (5), a nut (38) is connected to the micro ball screw motor (37), and the nut (38) is linked to the linear guide rail (23).

7. A printing method of the laser printer for pathological embedding cassettes according to claim 6, wherein the method comprises: transferring, by a host computer, a printing instruction to a printing control circuit (19); controlling, by the printing control circuit (19), a conveyor belt (6) to move, so as to move an embedding cassette (1) to a printing area; meanwhile, detecting, by a photoelectric sensor (10), the position of the embedding cassette (1), transferring, by the photoelectric sensor (10), detected position information of the embedding cassette (1) to the printing control circuit (19), and driving, by the printing control circuit (19) according to the information output by the photoelectric sensor (10), an ink jet cartridge (3) to eject ink droplets to the embedding cassette (1); and subsequently, driving, by the printing control circuit (19), a semiconductor laser (4) to irradiate the ink droplets with a laser beam, so that the ink droplets on the surface of the embedding cassette (1) have a rapid increase in temperature and are cured, wherein after the temperature of the cured ink droplets reach a melting point of plastic, the ink droplets are melted on a surface layer of plastic and integrated with plastic.

8. A printing method of the laser printer for pathological embedding cassettes according to claim 1, wherein the method comprises: transferring, by a host computer, a printing instruction to a printing control circuit (19); controlling, by the printing control circuit (19), a conveyor belt (6) to move, so as to move an embedding cassette (1) to a printing area; meanwhile, detecting, by a photoelectric sensor (10), the position of the embedding cassette (1), transferring, by the photoelectric sensor (10), detected position information of the embedding cassette (1) to the printing control circuit (19), and driving, by the printing control circuit (19) according to the information output by the photoelectric sensor (10), an ink jet cartridge (3) to eject ink droplets to the embedding cassette (1); and subsequently, driving, by the printing control circuit (19), a semiconductor laser (4) to irradiate the ink droplets with a laser beam, so that the ink droplets on the surface of the embedding cassette (1) have a rapid increase in temperature and are cured, wherein after the temperature of the cured ink droplets reach a melting point of plastic, the ink droplets are melted on a surface layer of plastic and integrated with plastic.

\* \* \* \* \*